United States Patent [19]
Merritt et al.

[11] Patent Number: 6,117,883
[45] Date of Patent: Sep. 12, 2000

[54] HETEROCYCLIC COMPOUNDS

[75] Inventors: Leander Merritt, Indianapolis; Jon K Reel, Carmel; Celia A Whitesitt; Richard L Simon, both of Greenwood, all of Ind.

[73] Assignee: Eli Lilly and Company, Indianapolis, Ind.

[21] Appl. No.: 09/171,794

[22] PCT Filed: Apr. 23, 1997

[86] PCT No.: PCT/US97/06699

§ 371 Date: Aug. 30, 1999

§ 102(e) Date: Aug. 30, 1999

[87] PCT Pub. No.: WO97/40044

PCT Pub. Date: Oct. 30, 1997

Related U.S. Application Data

[60] Provisional application No. 60/016,008, Apr. 23, 1996.

[51] Int. Cl.[7] .................. A61K 31/44; A61K 31/445; C07D 453/02; C07D 401/00; C07D 221/02

[52] U.S. Cl. .................. 514/305; 514/326; 514/299; 546/133; 546/137; 546/210; 546/112

[58] Field of Search .................. 546/137, 210, 546/112, 133; 514/305, 326, 299

[56] References Cited

U.S. PATENT DOCUMENTS

| | | | |
|---|---|---|---|
| 5,605,908 | 2/1997 | Merritt et al. | 514/305 |
| 5,646,289 | 7/1997 | Alt et al. | 548/110 |
| 5,852,037 | 12/1998 | Bodick et al. | 514/305 |
| 5,998,434 | 12/1999 | Mitch et al. | 514/305 |

FOREIGN PATENT DOCUMENTS

97/34899  9/1997  WIPO .

*Primary Examiner*—Deborah C. Lambkin
*Attorney, Agent, or Firm*—David M. Stemerick; Arleen Palmberg; Macharri Vorndran-Jones

[57] ABSTRACT

The present invention provides heterocyclic compounds which are useful for modulating a muscarinic receptor.

12 Claims, No Drawings

HETEROCYCLIC COMPOUNDS

Provisional Appln No. 60/016,008 filed Apr. 23, 1996.

The present invention relates to therapeutically active heterocyclic compounds having surprising potency at a muscarinic receptor. The novel compounds are useful as stimulants of the cognitive function of the forebrain and hippocampus of mammals.

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease, in halting its progression, and in improving the cognitive functions of elderly people.

Compounds active at a muscarinic cholinergic receptor are also useful analgesic agents and therefore are useful in the treatment of severely painful conditions.

Furthermore, muscarinic cholinergic receptor active compounds are useful in the treatment of glaucoma, psychosis, anxiety, mania, bipolar disorder, schizophrenia or schizophreniform conditions, depression, sleeping disorders, epilepsy, cerebral ischemia, and gastrointestinal motility disorders.

Therefore, new compounds having muscarinic cholinergic activity are desired. Some muscarinic cholinergic receptor active compounds are associated with side effects attributed to undesired modulation of the muscarinic cholinergic receptors, for example, such undesired modulation may cause excessive salivation and gastrointestinal upset. Thus, the most desired muscarinic cholinergic compounds shall have high potency and at the same time a favorable side effect profile, including a low incidence of excessive salivation.

The presently claimed compounds having a cyclopropanemethoxy substituent are surprisingly potent as $M_1$ agonists and provide a favorable side effect profile.

This invention provides compounds of the formula I:

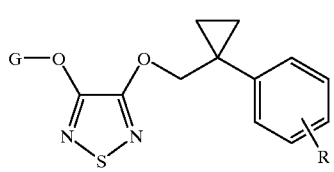

(I)

wherein

R is selected from the group consisting of hydrogen, —CN, halogen, —$CF_3$ and $R^4$;

$R^4$ is selected from the group consisting of $C_{1-6}$-alkyl, $C_{2-6}$-alkenyl and $C_{2-6}$-alkynyl, each of which is optionally substituted with one or more independently selected from the group consisting of halogen(s), —$CF_3$, and —CN;

G is selected from one of the following azacyclic or azabicyclic ring systems:

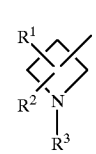

het-1

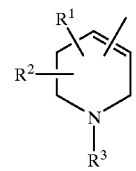

het-2

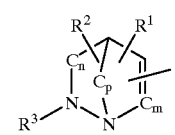

het-3

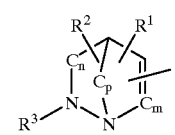

het-4

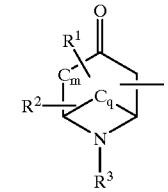

het-5

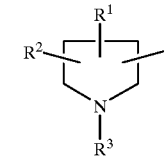

het-6

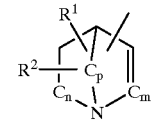

het-7

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —OH, —$COR^{6'}$, $CH_2$—OH, halogen, —$NH_2$, carboxy, unsubstituted phenyl and phenyl substituted at any position with $R^{6'}$;

$R^{6'}$ is hydrogen, $C_{1-6}$-alkyl;

$R^3$ is selected from the group consisting of hydrogen, $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

........ is a single or double bond;

It is an object of the invention to provide new muscarinic cholinergic compounds having surprising potency as M–1 receptor active compounds and a favorable side effect profile.

It is to be understood that the invention extends to each of the stereoisomeric forms of the compounds of the present invention as well as the pure diastereomeric, pure enatiomeric, and racemic forms of the compounds of this invention.

As used herein the term "treating" includes prophylaxis of a physical and/or mental condition or amelioration or elimination of the developed physical and/or mental condition once it has been established or alleviation of the characteristic symptoms of such condition.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

As used herein, the term "$h^+$" shall mean an alkoxide metal. As used herein, the term "alkoxide metal" means a metal suitable for alkoxide formation. Such alkoxide metals include, but are not limited to, $Li^+$, $K^+$, $Na^+$, $Cs^+$, and $Ca^{++}$. Especially preferred alkoxide metals include $Li^+$, $K^+$, and $Na^+$.

As used herein, the term "halogen" means Cl, Br, F, and I.

As used herein the phrase "one or more selected from" shall more preferredly refer to from 1–3 substituents. The term shall further preferredly refer to from 1–2 substituents.

The terms "$C_1$–$C_{n'}$ alkyl" wherein n' can be from 2 through 6, as used herein, represent a branched or linear alkyl group having from one to the specified number of carbon atoms. Typical $C_1$–$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$–$C_{n'}$ alkenyl" wherein n' can be from 3 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$–$C_5$ alkynyl" refers to an unsaturated branched or linear group having from 2 to 5 carbon atoms and at least one triple bond. Examples of such groups include, but are not limited to, 1-propynyl, 2-propynyl, 1-butynyl, 2-butynyl, 1-pentynyl, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "$C_5$–$C_8$ cycloalkenyl" represents an olefinically unsaturated ring having five to eight carbon atoms. Such groups include, but are not limited to, cyclohexyl-1,3-dienyl, cyclohexenyl, cyclopentenyl, cycloheptenyl, cyclooctenyl, cyclohexyl-1,4-dienyl, cycloheptyl-1,4-dienyl, cyclooctyl-1,3,5-trienyl and the like.

As used herein the term "carboxy" refers to a substituent having the common meaning understood by the skilled artisan, wherein the point of attachment may be through the carbon or oxygen atom of the group.

As used herein the term "aryl" means an organic radical derived from an aromatic hydrocarbon by the removal of one atom; e.g., phenyl or naphthyl. Most preferably, aryl refers to $C_6$–$C_{10}$ aryl, wherein the aryl ring system, including any alkyl substitutions, comprises from 6 to 10 carbon atoms; e.g., phenyl, 3,3-dimethylphenyl, naphthyl, and the like. The aryl radical may be substituted by one or two $C_1$–$C_6$ straight or branched alkyl. The term "aryl($C_1$–$C_3$) alkyl" refers to any aryl group which is attached to the parent moiety via the alkyl group.

The phrase "5-membered heterocycle" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles).

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science,* 66, 2 (1977) which are known to the skilled artisan. The compounds of this invention may form solvates with standard low molecular weight solvents using methods known to the skilled artisan.

The compounds of this invention can be prepared using the chemical processes illustrated in Scheme I. The starting materials for the illustrated process are commercially available or may be prepared using methods known to the skilled artisan.

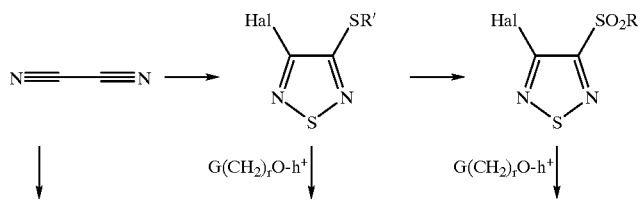

-continued

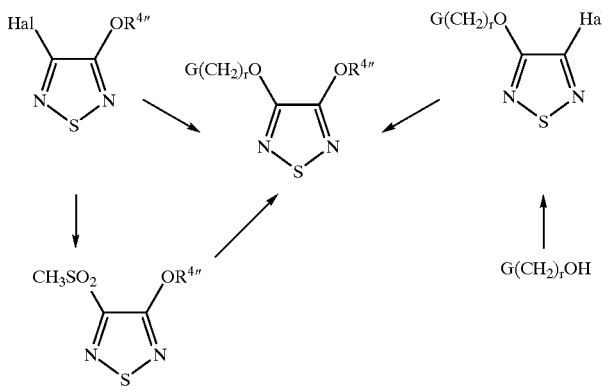

As used in Scheme I, h+ and G are as defined supra. As used in Scheme I, the term "Hal" refers to Cl, Br, and $R^9SO_2$. $R^9$ is $C_{1-8}$ straight or branched chain alkyl or aryl; R' is hydrogen, amino, halogen, alkyl, amino, and the like. As used in Scheme I, $R^{4''}$ is a group of the formula:

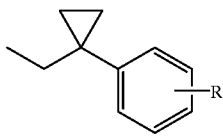

Preferred oxidizing agents for the process of Scheme I include oxone and sodium periodate. Oxone is an especially preferred oxidizing agent for the process of Scheme I. The artisan will appreciate that there may be additional process approaches for the preparation of compounds provided by this invention. See for example, U.S. Pat. No. 5,043,345, herein incorporated by reference in its entirety.

Certain intermediates of the present invention may be prepared using the process illustrated in Scheme IV.

Scheme IV

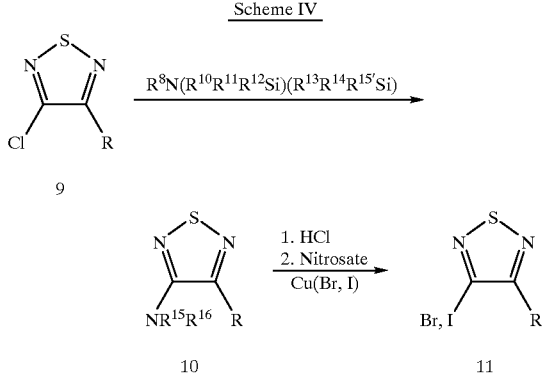

As used in Scheme IV, $R^8$ is Li, Na, or K; Si means silyl; $R^{10}, R^{11}, R^{12}, R^{13}, R^{14}$ and $R^{15'}$ are independently selected from the group consisting of $(C_1-C_6)$-alkyl, aryl, and aryl $(C_1-C_3)$alkyl; $R^{15}$ and $R^{16}$ are independently selected from the group consisting of hydrogen, $R^{10}R^{11}R^{12}Si$, and $R^{13}R^{14}R^{15'}Si$. R is selected from the group consisting of hydrogen, amino, halogen, $NHR^6$, $NR^6R^7$, $R^4$, —$OR^4$, —$SR^4$, —$SOR^4$, —$SO_2R^4$, $C_{3-10}$-cycloalkyl, $C_{4-12}$-(cycloalkylalkyl), —Z—$C_{3-10}$-cycloalkyl and —Z—$C_{4-12}$-(cycloalkylalkyl) wherein $R^4$ is $C_{1-15}$-alkyl, $C_{2-15}$-alkenyl, $C_{2-15}$-alkynyl, each of which is optionally substituted with one or more halogen(s), —$CF_3$, —CN, Y, phenyl or phenoxy wherein phenyl or phenoxy is optionally substituted with halogen, —CN, $C_{1-4}$-alkyl, $C_{1-4}$-alkoxy, —$OCF_3$, —$CF_3$, —$CONH_2$ or —$CSNH_2$; or R is phenyl or benzyloxycarbonyl, each of which is optionally substituted with halogen, —CN, $C_{1-4}$-alkyl, $C_{1-4}$-alkoxy, —$OCF_3$, —$CF_3$, —$CONH_2$ or —$CSNH_2$; or R is —$OR^5Y$, —$SR^5Y$, $OR^5$—Z—Y, —$SR^5ZY$, —O—$R^5$—Z—$R^4$ or —S—$R^5$—Z—$R^4$ wherein Z is oxygen or sulphur, $R^5$ is $C_{1-15}$-alkyl, $C_{2-15}$-alkenyl, $C_{2-15}$-alkynyl, and Y is a 5 or 6 membered heterocyclic group;

$R^6$ and $R^7$ independently are hydrogen, $C_{1-6}$-alkyl; or $R^6$ and $R^7$ together with the nitrogen atom optionally form a 4- to 6-member ring;

Z is oxygen or sulphur, $R^5$ is $C_{1-15}$-alkyl, $C_{2-15}$-alkenyl, $C_{2-15}$-alkynyl, and Y is a 5 or 6 membered heterocyclic group.

For example, $R^8N[(R^{10}R^{11}R^{12}Si)(R^{13}R^{14}R^{15'}Si)$ may be, but is not limited to lithium bis(tri-2-propylsilyl)amide, sodium bis(trimethylsilyl)amide, potassium bis(trimethylsilyl)amide, lithium bis(tri-2-propylsilyl)amide, sodium bis(ethyldimethylsilyl)amide, potassium bis(1-propylethylmethylsilyl)amide, lithium bis(tri-phenylsilyl)amide, sodium bis(tri-phenylmethylsilyl)amide, potassium bis(2-butyl-2-propylmethylsilyl)amide, lithium(tri-2-propylsilyl)(2-butyldiethylsilyl)amide, sodium (trimethylsilyl)(triphenylsilyl)amide, potassium(dimethyl phenylsilyl)(ethyldimethylsilyl)amide, and the like. Most preferably, $R^{15}$ and $R^{16}$ are each hydrogen when the process of Scheme III is used for preparing a compound of 11 from a compound of 10. The intermediate 10 may be nitrosated using standard nitrosating procedures. A preferred nitrosating agent is isoamyl nitrite; however, other known nitrosating agents are appropriate. As used in Scheme III, the term "Cu(Br,I)" refers to copper (I) bromide, copper (II) bromide, or copper (I) iodide. The artisan will recognize that the copper (I) bromide, copper (II) bromide, or copper (I) iodide reagent shall determine the substitution on the product of the process illustrated in Scheme III.

Certain compounds of this invention may more preferably be prepared by a process using a hydroxyalkylamine (G—OH) wherein G has the meaning defined supra. in the presence of a phosphorus(III) compound and a diester of azodicarboxylate to give the 1,2,5-thiadiazoyloxyalkylamine as illustrated by Scheme V.

Scheme V

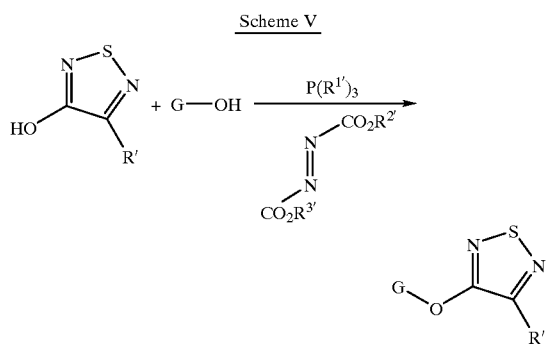

As used in Scheme IV, the R' is selected from the formula:

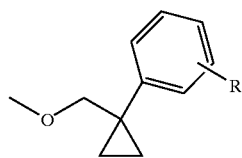

The term "G" is as defined herein above. $R^{1'}$ is selected from the group consisting of phenyl, $C_{1-15}$-alkyl, $C_{2-5}$-alkenyl, $C_{2-5}$-alkynyl and $(NR^{2'})_3$; $R^{2'}$ and $R^{3'}$ are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl. The process of Scheme IV is particularly advantageous because the process provides a method for inverting the stereochemistry at the carbon bearing the hydroxyl group in G.

Another new process illustrated by Scheme VI, involves the sequential reaction of 3,4-dihydroxy-1,2,5-thiadiazole with G—OH wherein G is defined as defined supra. in the presence of a phosphorous(III) compounds and a diester of azodicarboxylate to give an unisolated hydroxy-1,2,5-thiadiazole ether I" followed by reaction of I" with $R^4OH$ where $R^4$ is defined as supra. with phosphorous(III) compounds and a diester of azodicarboxylate to give the diethers of 3,4-dihydroxy-1,2,5-thiadiazole which are useful as muscarinic agonists and antagonists. (See, *Org. Prep. & Procedures* 1969, 1, 255–258) The substituents illustrated in Scheme VI are as defined supra.

Scheme VI

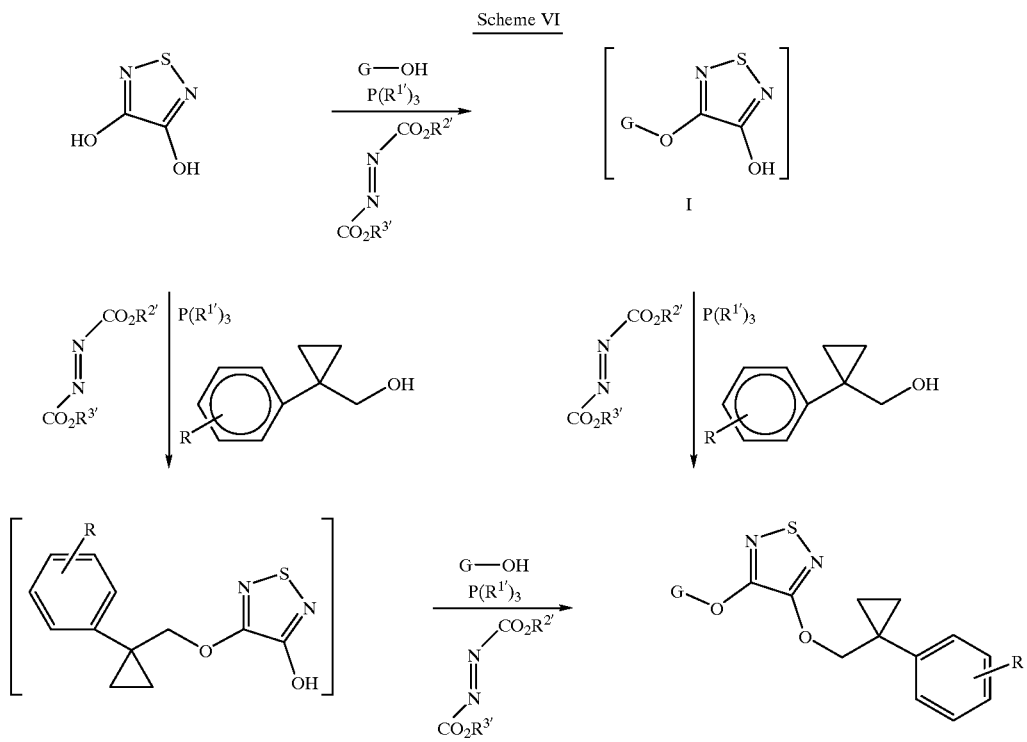

Alternatively, the order of addition of the alcohols may be reversed as shown above to give unisolated hydroxy-1,2,5-thiadiazole ether II which is subsequently converted to the same final muscarinic active compound.

Another process of this invention, illustrated by Scheme VIII, is the synthesis of 3-hydroxy-4-alkylthio-1,2,5-thiadiazoles by treating 3-halo-4-alkylthio-1,2,5-thiadiazoles with aqueous alkaline metal hydroxides in the presence or absence of a dipolar aprotic solvent. In this scheme, Hal has the meanings defined supra. and M is an alkoxide metal.

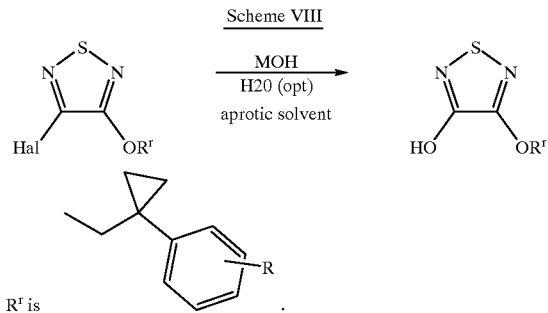

Scheme VIII

The compounds (11) are useful intermediates for the preparation of 1,2,5-thiadiazole compounds. The artisan will recognize that the intermediates 11 are useful for preparing 1,2,5-thiadiazole compounds as illustrated by the processes of Schemes I, II, and III.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis,* (John Wiley & Sons, New York, 1981).

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

As used herein the term "malfunctioning of the muscarinic cholinergic system" shall have the meaning accepted by the skilled artisan. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of $^3$H-Oxotremorine-M ($^3$H-Oxo). Birdsall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 seconds in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%). $IC_{50}$=(applied test substance concentration)×($C_x$/$C_o$-$C_x$)nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 μl of test solution and 25 μL of $^3$HPRZ (1.0 nM, final conc.), mixed and incubated for 60 min. at 20° C. Non-specific binding is determined in triplicate using atropine (1 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%). $IC_{50}$=(applied test substance concentration)$\times(C_x/C_o-C_x)$nM where $C_o$ is specific binding in control assays and $C_x$ is the specific binding in the test assay. (The calculations assume normal mass-action kinetics).

Stimulation of Phosphoinositol Hydrolysis in A9 L-ml Cells

A9-L-ml cells were cultured to confluence in 75 mL flasks containing Dubecco's modified essential media. Cells were prelabeled with 1 μCi/mL of myo[2-3H]inositol (Amersham Inc, 16.3 Ci/mmol) for 48 h prior to assay. On the day of assay, cells were detached using a 30 s exposure to 0.25% trypsin in 1 mM EDTA. The cells were collected by centrifugation (300×g for 5 min) and resuspended in oxygenated HEPES buffer containing 10 mM LiCl, 142 mM NaCl, 5.6 mM KCl, 2.2 mM $CaCl_2$, 1 mM $MgCl_2$, 3.6 mM $NaHCO_3$, 5.6 mM D-glucose, and 30 mM sodium HEPES at pH 7.4. Cells were incubated at 37 C. for 45 min in the presence of varying concentrations of drug. The reaction was terminated by the addition of 3 mL of ice cold 10 mM LiCl, sonicated, and centrifugated at 20,000×g. The supernatent was decanted over a Accell QMA anoin exchange SEP-PAK cartridge in the formate form (Waters Associates, Milford, Mass.). The cartridges were washed with 10 mL of $H_2O$ followed by 10 mL of 5 mM sodium borate. [3H]PI was eluted directly into scintillation vials for counting with 4 mL of 0.1 ammonium formate/0.01 mM formic acid/5 mM sodium borate. Data is expressed as the percent of total [3H]PI stimulated in the presence of 1 mM carbachol. Half-maximal values (EC50) were determined from the mean of seven point curves using a four parameter logistic model.

Additionally, the pharmacological activity and tendency to produce salivation can be determined using the following methods:

Salivation in Mice

Mice weighing 20 to 30 g were used for salivation testing. Mice, in groups of five, were injected i.p. with 10 mg/kg doses of compound dissolved in distilled water. After, 30 min, salivation and tremor were scored on a scale of 0, 1, or 2, where 0=no effect, 1=moderate salivation or tremor, and 2=marked salivation or tremor. Those compounds producing an average score of 1 were tested at half log lower doses until a score lower than 1 was achieved. The lowest dose of compound producing a score of 1 was expressed at the minimum effective dose (MED).

Table I illustrates several additional formula I compounds as claimed herein.

TABLE I

| R | G | R | G |
|---|---|---|---|
| p-Cl | 3.2.1 azabicycle | p-Cl | 2-aza-[2.2.1]heptane |
| p-F | 3.2.1 azabicycle | p-F | 2-aza-[2.2.1]heptane |
| p-CN | 3.2.1 azabicycle | p-CN | 2-aza-[2.2.1]heptane |
| p-CH$_3$ | 3 2 1 azabicycle | p-CN | 2-aza-[2.2.1]heptane |
| p-Cl | 2.2.2 azabicycle | m-Cl | 3.2.1 azabicycle |
| p-Cl | 3-piperidyl | m-CF$_3$ | 2-aza-[2.2.1]heptane |
| p-F | 3-piperidyl | m-CN | 2.2.2 azabicycle |

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

In order to more fully illustrate the operation of this invention, the following formulation examples are provided. The examples are illustrative only, and are not intended to limit the scope of the invention in any way.

Formulation 1

A typical tablet, appropriate for use in this method, may be prepared using conventional techniques and may contain:

|  | Amount per Tablet | Concentration by Weight (%) |
|---|---|---|
| 3-(1-(4-fluorophenyl)-1-cyclopropanemethoxy))-4-(1-azabicyclo[2.2.2]octyl-3-oxy)-1,2,5-thiadiazole | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg | 0.3 |
|  | 105.45 mg | 100 |

Formulation 2

Hard gelatin capsules are prepared using the following ingredients:

|  | Amount per Tablet | Concentration by Weight (%) |
|---|---|---|
| 3-(1-(4-chlorophenyl)-1-cyclopropanemethoxy))-4-(1-azabicyclo[3.2.1]octyl-3-oxy)-1,2,5-thiadiazole | 0.1 mg | 0.05 |
| starch dried | 200 mg | 95.2 |
| magnesium stearate | 10 mg | 4.8 |
|  | 210.1 mg | 100 |

The above ingredients are mixed and filled into hard gelatin capsules in 210.1 mg quantities.

Formulation 3

Suspensions each containing 1 mg of medicament per 5 mL dose are as follows:

|  | Amount per 5 mL of suspension |
|---|---|
| 3-(1-(4-chlorophenyl)-1-cyclopropanemethoxy))-4-(1-azabicyclo[2.2.2]octyl-3-oxy)-1,2,5-thiadiazole | 1 mg |
| sodium carboxymethyl cellulose | 50 mg |
| syrup | 1.25 mL |

-continued

|  | Amount per 5 mL of suspension |
|---|---|
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The intermediates and processes of the present invention are useful for preparing compounds having beneficial muscarinic receptor activity. The compounds of the present invention have such useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:

A) G is 1-azabicyclo[2.2.2]octyl;
B) R is c;
C) G is azabicyclic 3.2.1
D) R is selected from Cl and F;
E) R is F.

The invention will now be described in further detail with reference to the following examples. The examples are provided for illustrative purposes, and are not to be construed as limiting the scope of the invention in any way.

EXAMPLE 1

(±)-3-(1-(4-Chlorophenyl)-1-cyclopropanemethoxy))-4-(1-azabicyclo[2.2.2]octyl-3-oxy)-1,2,5-thiadiazole A solution of 1-(4-chlorophenyl)-1-cyclopropanemethanol (0.47 g) in THF (20 mL) was treated with potassium tert-butoxide (0.30 g). After 1.5 h., a solution of 3-propylsulfonyl-4-(1-azabicyclo[2.2.2]octyl-3-oxy)-1,2,5-thiadiazole (0.40 g) in THF (10 mL) was added dropwise to the reaction and the mixture was stirred 4.5 h. This reaction mixture was quenched with water and extracted with ether. The residue was purified by radial chromatography (5% EtOH-0.5% NH$_4$OH—CHCl$_3$) to give 0.41 free base. The HCl salt (0.36 g) crystallized from chloroform-ether, m.p.139–141° C.

EXAMPLE 2

(5R, 6R)-endo-3-[1-(4-fluorophenyl)cyclopropylmethoxyl-4-(1-azabicyclo[3.2.1]octyl-6-oxy-1,2,5-thiadizole (357900, Lot # 539-FCN-11)

1-(4-fluorophenyl)cyclopropylnitrile. 4-fluorophenylacetonitrile (27.0 g, 0.2 m) was added to a stirred suspension of lithium amide (27.0 g, 1.17 m) in 270 ml ethylene glycol diethyl ether. Added slowly dropwise was 54 ml of 1,2-dibromoethane and the reaction stirred for 16 hr. Ethyl acetate was added and the solution washed thoroughly with water. The solution was dried, condensed and purified by HPLC over silica gel eluted with 10% EtOAc/hexane to yield 9.1 g (26%) of product. Mass spec 161.

1-(4-fluorophenyl)cyclopropylformaldehyde. DiBAl (71 ml of 1 M solution) was added to a stirred solution of 1-(4-fluorophenyl)cyclopropylnitrile (9.1 g, 0.056 m) in 200 ml toluene and stirred for 1.5 hr. The reaction was cooled and 6 ml MeOH and 94 ml of saturated potassium sodium tartrate added. The toluene layer was washed with water, 1N NaOH, $H_2SO_4$ and water then dried and condensed to yield 6.3 g (68%) of product. Mass spec 180.

1-(4-fluorophenyl)cyclopropylmethanol. Sodium borohydride (1.7 g, 0.045 m) was added portion wise at 0° C. to as stirred solution of 1-(4-fluorophenyl)cyclopropylformaldehyde in 500 ml methanol and stirred at room temperature overnight. The reaction was condensed, EtOAc added, washed with water, dried and condensed to yield 6.1 g (97%). Mass Spec 166.

(5R, 6R)-endo-3-[1-(4-fluorophenyl)cyclopropylmethoxy]-4-(1-azabicyclo[3.2.1]octyl-6-oxy-1,2,5-thiadizole. 1-(4-fluorophenyl)cyclopropylmethanol (0.48 g, 2.9 mmol) was added at –40° C. to a stirred solution of potassium t-butoxide (0.34 g, 3.0 mmol) in 50 ml THF. After stirring for 15 min, (5R, 6R)-endo-propylsulfonyl-4-(1-azabicyclo[3.2.1]octyl-6-oxy)-1,2,5-thiadizole (0.6 g, 1.9 mmol) was added and the solution stirred for an additional 30 min. The reaction was quenched with water and the product extracted with EtOAc, dried and condensed. The product was purified by HPLC over silica gel eluted with $CHCL_3$/EtOH/$NH_4OH$, 50/49/1 and converted to the hydrochloride salt to yield 0.6 g (78%) of product.

The following compounds were prepared using substantially the same procedure as described in Example 3.

EXAMPLE 3

344070, (±), p-chlorophenylcyclopropylethanol, maleate, lot # M52-FBA-116, m.pt 104–1050, yield 21%.

EXAMPLE 4

350125, (5R, 6R), p-chlorophenylcyclopropylethanol, maleate, lot # M52-FBA-259, m.pt 114–1150, yield 63%

EXAMPLE 5

344911, 3-[1-(4-chlorophenyl)cyclopropylmethoxy]-4-(2-azabicyclo[2.2.1]heptyl-6-oxy-1,2,5-thiadiazole was prepared in a similar procedure from 3-(n-propylsulfonyl)-4-(2-azabicyclo[2.2.1]heptyl-6-oxy-1,2,5-thiadiazole (see preparation from 2-aza{2.2.1]docket), maleate, lot #M52-FBA-213, m.pt. 119–1200, yield 49%

EXAMPLE 6

344738 R-3-[1-(4-chlorophenyl)cyclopropylmethoxy]-4-(3-piperidinyloxy)-1,2,5-thiadiazole (lot #M52-FBA-212).

R-3-hydroxy-1-t-butoxycarbonylpiperidine. Di-t-butylcarbonate (9.5 g, 0.044 m) was added to a solution of R-3-hydroxypiperidine hydrochloride (5.0 g, 0.036 m) and potassium carbonate (12.0 g, .086 m) in 140 ml of a 50% solution of THF in water and stirred for 4 hr. EtOAc was added and the solution washed with water, dried and condensed to yield 6.6 g (92%) of R-3-hydroxy-1-t-butoxycarbonylpiperidine.

3-(N-t-Butyloxycarbonyl-3-piperidyloxy)-4-n-propylthiothiadiazole. 3 g of R-3-hydroxy-1-t-BOC-piperidine (0.015 m) was added to a stirred solution of potassium t-butoxide (1.66 g, 0.015 m) in 80 ml THF and cooled to 0–5° C. After stirring for 15 min., 3-chloro-4-n-propylthio-1,2,5-thiadiazole (3.05 g, 0.016 m) was added and the reaction warmed to room temperature, stirred for 3 hr, poured into EtOAc and washed with water. The organic layer was dried, concentrated and purified by HPLC over silica gel eluted with 50/49/1 $CHCl_3$/EtOH/$NH_4OH$ to yield 3.3 g (62%) of product. Mass spec (FD) 359.

3-(R-3-piperidyloxy)-4-n-propylsulfonylthiadiazole. The 3.3 g of thiadizole (9 mmol) was stirred at 0° C. with oxone (22.5 g, 36 mmol) in 200 ml water and 200 ml THF, allowed to warm to room temperature and stirred for 4 hrs. Sodium bisulfite was added until a negative starch iodide test was obtained. EtOAc was added, the solution washed with water, dried and condensed to yield 3.2 g (91%) of product. The t-BOC (3.3 g, 8 mmol) was cleaved by stirring at 0° C. with trifluoroacetic acid (9.1 g, 80 mmol) in 50 ml methylenechloride and stirring at room temperature for 16 hr. The solution was dissolved in EtOAc, washed with water and acidified and 5N HCl. EtOAc was added to the aqueous solution, the pH adjusted to 9 with 5 N NaOH, the organic layer dried and condensed to yield 1.3 g (56%) of product. Mass spec (FD) 291. C,H,N.

3-(R-3-piperidyloxy)-4-(1-(4-chlorophenyl)cyclopropylmethoxy)-1,2,5-thiadiazole. 1-(4-chlorophenyl)cyclopropylmethanol (1.36 g, 7.5 mmol) was added at ice bath temperature to potassium t-butoxide (0.84 g, 7.5 mmol) in 60 ml THF, cooled to –78° C. and 3-(R-3-piperidyloxy)-4-n-propylsulfonylthiadiazole (0.065 g, 2.5 mmole) added and stirred for 2 hr. EtOAc and water were added, the pH adjusted to 2.0 with 1 N HCl, EtOAc added to the aqueous layer, pH adjusted to 12, the organic layer dried and evaporated to yield 660 mg (60%) of the maleate salt of product , m.pt 130–131° C. Mass spec (FD) 366.3.

What is claimed is:

1. A compound of formula I of the formula I:

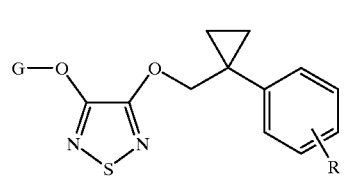

wherein

R is selected from the group consisting of hydrogen, —CN, halogen, —$CF_3$ and $R^4$;

$R^4$ is selected from the group consisting of $C_{1-16}$-alkyl, $C_{2-16}$-alkenyl and $C_{2-16}$-alkynyl, each of which is optionally substituted with one or more independently selected from the group consisting of halogen(s), –$CF_3$, and —CN;

G is selected from one of the following azacyclic or azabicyclic ring systems:

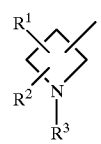

het-1

-continued het-2
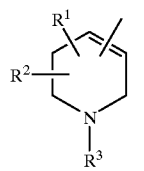

het-3
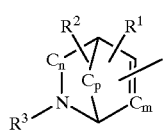

het-4
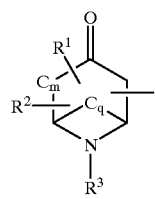

het-5
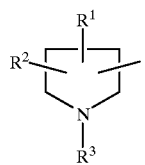

het-6
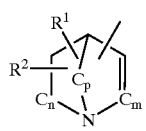

het-7
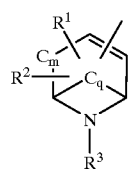

$R^1$ and $R^2$ independently are selected from the group consisting of hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —OH, —$COR^{6'}$, $CH_2$—OH, halogen, —$NH_2$, carboxy, and phenyl;

$R^{6'}$ is hydrogen, $C_{1-6}$-alkyl;

$R^3$ is selected from the group consisting of hydrogen, $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

……… is a single or double bond.

2. A compound of claim 1 wherein G is 1-azabicyclo[3.2.1]octyl.

3. A compound of claim 1 wherein R is selected from the group consisting of Cl and F.

4. A compound of claim 3 wherein R is in the para position.

5. A compound of claim 1 wherein G is 2-azabicyclo[2.2.2]octyl.

6. A compound of claim 5 wherein R is selected from the group consisting of Cl and F.

7. A compound of claim 2 wherein R is selected from Cl and F.

8. A formulation comprising a compound of claim 1 associated with one or more carriers, diluents, or excipients therefor.

9. A method for modulating a muscarinic receptor comprising administering an effective amount of a compound of claim 1 to a patient in need thereof.

10. A method of claim 9 wherein the compound acts as a muscarinic receptor antagonist.

11. A method of claim 9 wherein the compound acts as a muscarinic receptor agonist.

12. A compound as claimed by claim 1 for use in the manufacture of a medicament.

* * * * *